US00PP26535P2

(12) United States Plant Patent
Hooijman

(10) Patent No.: US PP26,535 P2
(45) Date of Patent: Mar. 29, 2016

(54) ROSE PLANT NAMED 'ESM R177'

(50) Latin Name: *Rosa hybrida*
Varietal Denomination: ESM R177

(71) Applicant: Aloysius A. J. Hooijman, Aalsmeer (NL)

(72) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 76 days.

(21) Appl. No.: 14/120,580

(22) Filed: Jun. 6, 2014

(51) Int. Cl.
*A01H 5/02* (2006.01)

(52) U.S. Cl.
USPC ..... Plt./137

(58) Field of Classification Search
USPC ..... Plt./137, 107
CPC ..... A01H 5/0222; A01H 5/0216
See application file for complete search history.

*Primary Examiner* — Kent L Bell
(74) *Attorney, Agent, or Firm* — C. A. Whealy

(57) ABSTRACT

A new and distinct cultivar of Rose plant named 'ESM R177', characterized by its upright, long and strong flowering stems; vigorous growth habit and high productivity; brown-colored flowering stems; dark green-colored leaves; large flower buds; large light pink-colored flowers that are typically grown as single-stem types; and excellent postproduction longevity.

1 Drawing Sheet

Botanical designation: *Rosa hybrida.*
Cultivar denomination: 'ESM R177'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R177'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in March, 2009 of a proprietary Rose selection identified as Line 476, not patented, as the female, or seed, parent with a proprietary Rose selection identified as Line 432, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in June, 2010.

Asexual reproduction of the new Rose plant by bud grafting in El Quinche, Pichincha, Ecuador since September, 2010 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R177'.

These characteristics in combination distinguish 'ESM R177' as a new and distinct Rose plant:

1. Upright, long and strong flowering stems.
2. Vigorous growth habit and high productivity.
3. Brown-colored flowering stems.
4. Dark green-colored leaves.
5. Large flower buds.
6. Large light pink-colored flowers that are typically grown as single-stem types.
7. Excellent postproduction longevity.

Plants of the new Rose differ from plants of the female parent selection in the following characteristics:

1. Plants of the new Rose have longer flowering stems than plants of female parent selection.
2. Plants of the new Rose and the female parent selection differ in flower color as plants of the female parent selection have white-colored flowers.

Plants of the new Rose differ from plants of the male parent selection in the following characteristics:

1. Stems of plants of the new Rose had more thorns than stems of the male parent selection.
2. Plants of the new Rose have taller flower buds than plants of the male parent selection.
3. Flowers of plants of the new Rose have more petals than flowers of plants of the male parent selection.
4. Plants of the new Rose and the male parent selection differ in flower color as plants of the male parent selection have creamy white-colored flowers.
5. Flowers of plants of the new Rose are longer-lasting than flowers of plants of the male parent selection.

Plants of the new Rose can be compared to plants of Rose 'Charming Unique', not patented. In side-by-side comparisons conducted in El Quinche, Pichincha, Ecuador, plants of the new Rose differed from plants of 'Charming Unique' in the following characteristics:

1. Plants of the new Rose were taller and broader than plants of 'Charming Unique'.

2. Plants of the new Rose were more vigorous and produced more flowering stems than plants of 'Charming Unique'.
3. Stems of plants of the new Rose were stronger, thicker, darker in color and had more thorns than stems of plants of 'Charming Unique'.
4. Plants of the new Rose had larger leaves and leaflets than plants of 'Charming Unique'.
5. Plants of the new Rose had larger flower buds than plants of 'Charming Unique'.
6. Flowers of plants of the new Rose had more petals than flowers of plants of 'Charming Unique'.
7. Plants of the new Rose and 'Charming Unique' differed slightly in flower color.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph on the left side of the sheet comprises a side perspective views of a typical flowering stem of 'ESM R177'.

The photographs at the upper right of the sheet are close-up views of typical developing flowers of 'ESM R177'.

The photograph at the lower right of the sheet are close-up views of the upper and lower surfaces of typical leaves of 'ESM R177'.

DETAILED BOTANICAL DESCRIPTION

The aforementioned photographs, following observations and measurements describe plants grown in 10-liter containers in a polyethylene-covered greenhouse in El Quinche, Pichincha, Ecuador and under typical hydroponic Rose production practices. Plants were pinched 13 to 14 weeks after planting and were 109 weeks old when the description and photographs were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'ESM R177'.

Parentage:

*Female, or seed, parent*.—Proprietary seedling selection of *Rosa hybrida* identified Line 476, not patented.

*Male, or pollen, parent*.—Proprietary seedling selection of *Rosa hybrida* identified Line 432, not patented.

Propagation:

*Type*.—By bud grafting.

*Time to initiate roots, summer*.—About 15 days at temperatures about 26° C. to 30° C.

*Time to produce a rooted young plant, summer*.—About 30 days at temperatures about 22° C. to 26° C.

*Root description*.—Fibrous, medium in thickness; close to N200A in color.

*Rooting habit*.—Moderately freely branching; medium density.

Plant description:

*Plant and growth habit*.—Perennial shrub; upright and strong flowering stems; typically grown as a single-stem type cut flower; vigorous growth habit.

*Branching habit*.—Freely basal branching habit; highly productive with about 16 flowering stems developing per plant per year.

*Plant height*.—About 148 cm.

*Plant width* (*spread*).—About 61 cm.

*Lateral branches*.—Quantity: About eleven lateral branches develop per plant. Length: About 107 cm. Diameter: About 9 mm. Internode length: About 5.8 cm. Texture: Smooth, glabrous; older stems, woody. Color: Close to N199A and N200A. Thorns: Density: Medium to high. Shape: Triangular with sharp acuminate apices; slightly incurved and flat. Height: About 1.2 cm. Length, at base: About 8 mm. Color, immature: Close to 187C. Color, mature: Close to 187B.

Leaf description:

*Arrangement*.—Alternate; compound with typically seven leaflets per leaf.

*Leaf length*.—About 20.1 cm.

*Leaf width*.—About 14.4 cm.

*Terminal leaflet length*.—About 8.1 cm.

*Terminal leaflet width*.—About 4.8 cm.

*Lateral leaflet length*.—About 7.2 cm.

*Lateral leaflet width*.—About 4.3 cm.

*Leaflet shape*.—Ovate.

*Leaflet apex*.—Acute.

*Leaflet base*.—Attenuate.

*Leaflet margin*.—Serrate.

*Leaflet texture, upper and lower surfaces*.—Smooth, glabrous; papery to coriaceous.

*Leaflet venation pattern*.—Pinnate.

*Leaflet color*.—Developing leaflets, upper surface: Close to 139A. Developing leaflets, lower surface: Close to 146A. Fully expanded leaflets, upper surface: Close to 139A; venation, close to 148A. Fully expanded leaflets, lower surface: Close to 146A and 147B; venation, close to 199A and 152A.

*Petioles, leaves*.—Length: About 2.4 cm. Diameter: About 3 mm. Texture, upper surface: Prickly. Texture, lower surface: Smooth, glabrous. Color, upper surface: Close to 146A, 199B and 164A. Color, lower surface: Close to 146A to 146B.

*Petioles, leaflets*.—Length: About 1.6 cm. Diameter: About 2 mm. Texture, upper surface: Prickly. Texture, lower surface: Smooth, glabrous. Color, upper surface: Close to 146A and 187A. Color, lower surface: Close to 146A to 146C.

*Stipules*.—Arrangement and appearance: Two, adnate to the petiole, leafy in appearance. Length: About 3.1 cm. Width: About 2 mm. Shape: Roughly deltoid. Apex: Acuminate, tapered. Base: Tapered. Margin: Serrate. Texture, upper and lower surfaces: Smooth; membranous. Venation pattern: Pinnate. Color, upper surface: Close to 147A and 53A. Color, lower surface: Close to 146A.

Flower description:

*Flower type and arrangement*.—Symmetrical rosette flowers; flowers typically grown as single-stem types; flowers face upright.

*Flowering season*.—Plants of the new Rose flower year-round under greenhouse conditions; early flowering habit, plants begin flowering about 77 days after pinching; in the garden, optimal flowering from spring through autumn; flowering intermittent.

*Flower diameter*.—About 12.4 cm.

*Flower depth* (*height*).—About 6.5 cm.

*Flower longevity on plant*.—Excellent postproduction longevity, flowers maintain good substance for about 33 days; flowers persistent.

*Flower longevity as a cut flower*.—Excellent postproduction longevity, flowers last about ten to twelve days; flowers persistent.

*Fragrance*.—None detected.

*Flower buds*.—Shape: Ovoid. Length: About 7 cm. Diameter: About 5.4 cm. Color: Close to 146A and 175A.

*Petals*.—Quantity: About 30 to 34 per flower; petals imbricate. Length: About 6.5 cm. Width: About 7.4 cm. Shape: Broadly ovate. Apex: Shortly acute. Base: Obtuse. Margin: Entire. Texture, upper and lower surfaces: Smooth, glabrous; papery to coriaceous. Color: When opening, upper surface: Towards the apex and margins, close to N170D and 36A; center, close to 159C; towards the base, close to 160A. When opening, lower surface: Towards the apex and margins, close to 54C; center, close to N155C; towards the base, close to 154D. Fully opened, upper surface: Close to 56B; base and diffusing towards the center, close to 1B. Fully opened, lower surface: Close to 56A; towards the base, close to 154D.

*Petaloids*.—Quantity: About five; petaloids whorled. Length: Variable. Width: Variable. Shape: Irregularly shaped. Apex: Shortly acute. Base: Obtuse. Margin: Mostly uneven. Texture, upper and lower surfaces: Smooth, glabrous; papery to coriaceous. Color: When opening and fully opened, upper surface: Close to 67D; towards the base, close to 5A and 157D. When opening and fully opened, lower surface: Close to 50D; towards the base, close to 1B and 161D.

*Sepals*.—Quantity per flower: Typically five in a single whorl. Length: About 5.4 cm. Width: About 1.4 cm. Shape: Roughly deltoid. Apex: Tapered. Base: Truncate. Margin: Entire; ciliated and/or glandular. Texture, upper and lower surfaces: Leathery. Color: When opening, upper surface: Close to 146B to 146D. When opening, lower surface: Close to 146B to 146D and 165A. Fully opened, upper surface: Close to 146B to 146D. Fully opened, lower surface: Close to 146A to 146D and 175A.

*Reproductive organs*.—Stamens: Quantity: About 160 per flower. Anther length: About 4 mm. Anther shape: Reniform. Anther color: Close to 163B and 162B. Filament color: Close to 2C. Pollen amount: Moderate. Pollen color: Close to N199D. Pistils: Quantity: About 231 per flower. Pistil length: About 1.9 cm. Stigma shape: Broadly reniform. Stigma color: Close to 160A. Style length: About 1.3 cm. Style color: Close to 8D. Receptacle height: About 1.3 cm. Receptacle diameter: About 1.5 cm. Receptacle shape: Cup-shaped. Receptacle texture: Smooth, glabrous. Receptacle color: Close to 144A and 177B. Seeds: Seed production has not been observed to date on plants of the new Rose.

Pathogen & pest tolerance/resistance: Plants of the new Rose have not been observed to be resistant or tolerant to pathogens and pests common to Rose plants.

Temperature tolerance: Plants of the new Rose have been observed to tolerate temperatures ranging from 0° C. to 35° C.

It is claimed:

1. A new and distinct Rose plant named 'ESM R177' as illustrated and described.

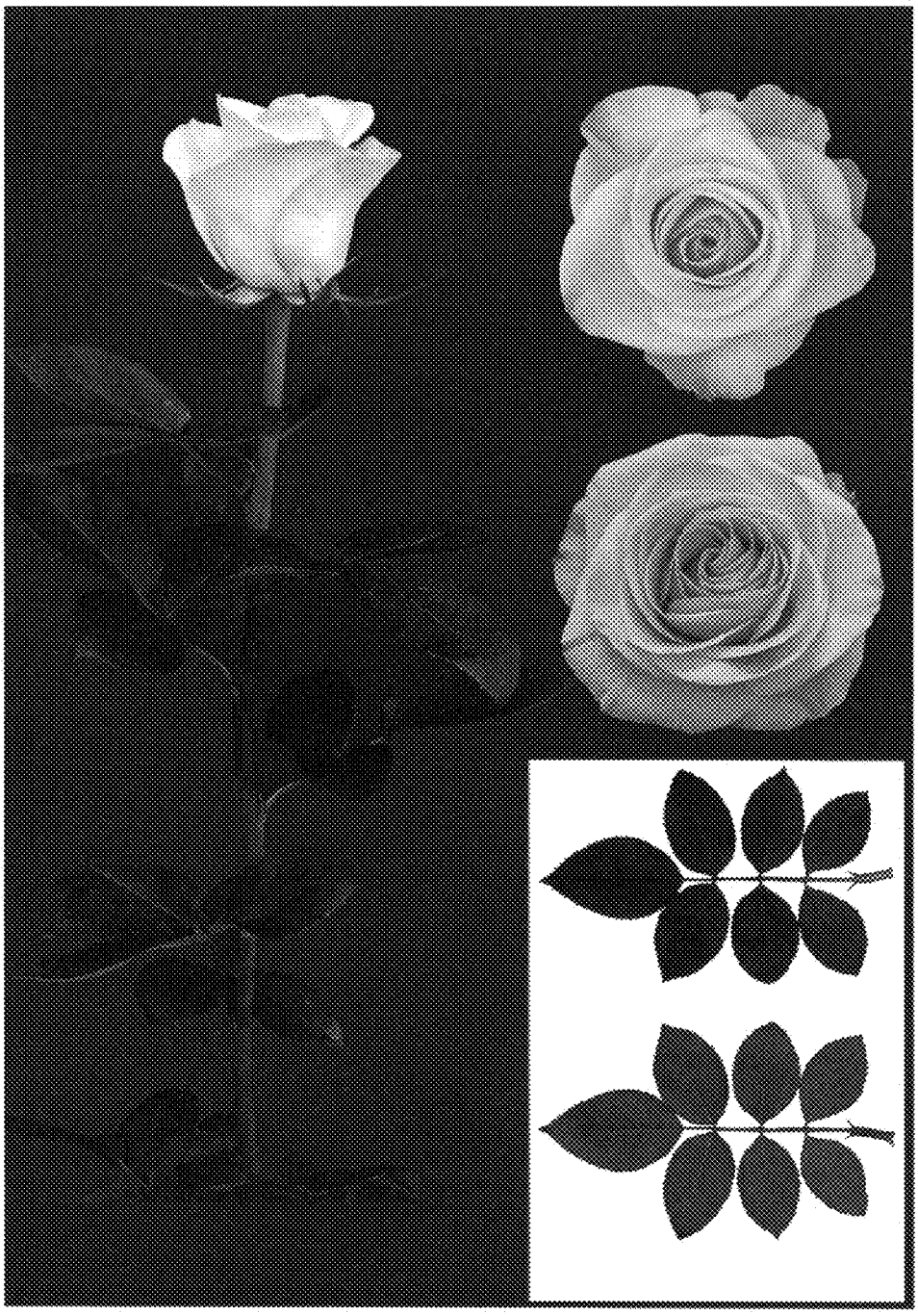

* * * * *